US00PP22729P3

(12) United States Plant Patent
Clough

(10) Patent No.: US PP22,729 P3
(45) Date of Patent: May 15, 2012

(54) PECAN TREE NAMED 'ECLIPSE'

(50) Latin Name: *Carya illinoinensis*
Varietal Denomination: ECLIPSE

(75) Inventor: Andrew L. Clough, Blackshear, GA (US)

(73) Assignee: Andrew L. Clough, Blackshear, GA (US)

( * ) Notice: Subject to any disclaimer, the term of this patent is extended or adjusted under 35 U.S.C. 154(b) by 104 days.

(21) Appl. No.: 12/803,893

(22) Filed: Jul. 9, 2010

(65) Prior Publication Data

US 2012/0011625 P1 Jan. 12, 2012

(51) Int. Cl.
*A01H 5/00* (2006.01)

(52) U.S. Cl. ..... Plt./153

(58) Field of Classification Search ..... Plt./153
See application file for complete search history.

(56) References Cited

OTHER PUBLICATIONS

MPEP Chapter 1600 Plant Patents Aug. 2001, 10 pages.*

* cited by examiner

*Primary Examiner* — June Hwu

(57) ABSTRACT

A new and distinct cultivar of pecan tree, *Carya illinoinensis,* which is characterized by extremely early nut maturity, high percentage kernel, moderate nut size, and scab fungus resistance.

5 Drawing Sheets

FIELD OF THE INVENTION

Figure 1:
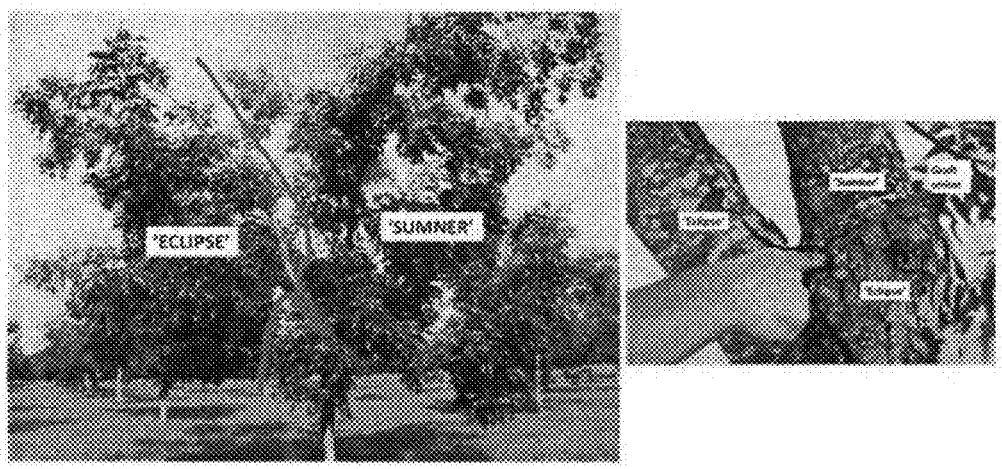

Disclosed herein is a new and distinct variety of pecan tree. Botanical classification: *Carya illinoinensis.* Varietal denomination: Pecan 'ECLIPSE'.

BACKGROUND OF THE INVENTION

The present invention relates to a new and distinct cultivar of the nut-bearing tree *Carya illinoinensis,* known as common pecan and hereafter referred to by the varietal denomination 'ECLIPSE'. It can be used in gardens or for commercial production of pecan nuts.

The tree was discovered by the inventor in a cultivated area on a farm in Pierce County, Ga. The tree was in a row planted as grafted trees of the cultivar 'Sumner' non-patented. The selection was clearly not 'Sumner' non-patented, as harvest date was more than 54 days earlier and nut shape and bark texture were clearly distinct. Since the tree was supposed to be 'Sumner' non-patented, the orchard manager grafted one limb to 'Sumner' non-patented (FIG. 1) in an attempt to convert the tree to that cultivar. Closer observation at the base of the tree revealed the absence of a graft union, indicating that the original tree was an ungrafted seedling, likely resulting from a failed graft attempt at the nursery. Andrew Clough, the inventor, noted exceptional characteristics exhibited on the part of the tree that remained ungrafted. The selection had exceptionally early harvest date, high nut quality, good productivity, and resistance to scab disease and other pests. He then asexually propagated the plant from this cultivated area.

Graft wood of the original 'ECLIPSE' tree has been propagated by the inventor by inlay bark grafting onto approximately 50 trees in test orchards in Pierce County, Ga. Additionally, wood was provided for testing purposes to Bill Goff, who propagated 12 'ECLIPSE' trees in a research planting near Tallassee, Ala. in spring, 2010. In all cases, all horticultural traits observed including leaf shape, color, and morphology, bud form, bark color and texture observed are identical to the parent tree, as is normal and expected when pecan trees are propagated by grafting.

Parentage of the tree is unknown. However, characteristics of the tree and nuts, and history of origin, lead to speculation that the parents may be 'Moore' non-patented×'Pawnee' non-patented. Nuts resemble 'Pawnee' non-patented, though earlier and more scab resistance. Bark color and texture resemble 'Moore' non-patented. 'Moore' non-patented was commonly used as a rootstock in nurseries, and the tree is thought to have originated from a tree bought from a nursery located in Lakeland, Ga., in 1993. The nursery graft either failed or the top died later, resulting in the current unique selection from the original rootstock tree. The tree was purchased to be a grafted 'Sumner' non-patented, and half of the tree was grafted to that variety about 2004. 'ECLIPSE' is obviously distinct from 'Sumner' non-patented as harvest date of 'Sumner' non-patented is about 54 days later than 'ECLIPSE'.

SUMMARY OF THE INVENTION

Plants of the cultivar 'ECLIPSE' have not been observed under all possible environmental conditions. The phenotype may vary somewhat with variations in environment such as light intensity, temperature and cultural conditions, without any variance in genotype.

The following characteristics have been consistently observed and, to the best knowledge of the inventor, their combination form unique characteristics of 'ECLIPSE' as a new and distinct cultivar:

Harvest date is very early, with 50% shuck split about Sept. 8 in Blackshear, Ga. This is about 18 days earlier than 'Pawnee' non-patented and 39 days earlier than 'Stuart' non-patented. No other known pecan cultivar has a harvest date this early and comparable nut size and quality. With marginal care (2 sprays) in 2009, a year of high scab incidence, and lower than normal nut size and quality in Georgia, a one-pound sample of nuts of 'ECLIPSE' from the parent tree had 61.4 nuts per pound and 55.6% kernel. The sample was collected and graded by Bill Goff. Productivity appears good and comparable to 'Pawnee' non-patented and 'Sumner' non-patented, based on observations of the 3 cultivars under similar growing conditions at the orchard where 'ECLIPSE' was discovered. Height of the tree at 12 years old was 27 feet with a canopy diameter of 29 feet. Diameter of the trunk at 12-inch height was 12.4 inches.

Some nuts at the base of a nut cluster have a characteristic long looping bract three to four times longer than the other 3 bracts on the same nut.

Bark is scaly, gray, and large flakes of 7 cm or more can be peeled from the trunk.

Resistance to scab is very good. In the same season under comparable conditions on adjacent trees, scab on the worst nut on the tree covered 3% of the nut shuck on 'ECLIPSE', compared to 8% on 'Sumner' non-patented and 100% on 'Pawnee' non-patented.

'ECLIPSE' trees were asexually reproduction by the inventor using inlay bark grafting onto approximately 50 trees in orchards on his farm at 3200 Clough Drive in Blackshear, Ga. The unique characteristics of this new pecan are stable and reproduced true-to-type in successive generations.

BRIEF DESCRIPTION OF PHOTOGRAPHS

FIG. 1. 'ECLIPSE' pecan tree, photographed Sep. 12, 2009, estimated to be 12 years old. 'ECLIPSE' grew from a seed. A limb on the tree was grafted to 'Sumner' non-patented, resulting in a portion of the tree converted to 'Sumner'. Note graft union in photograph on right. There is only one graft on the tree, with all portions distal to the graft being 'Sumner', and the rest of the tree, including trunk and roots, 'ECLIPSE'.

Figure 2:
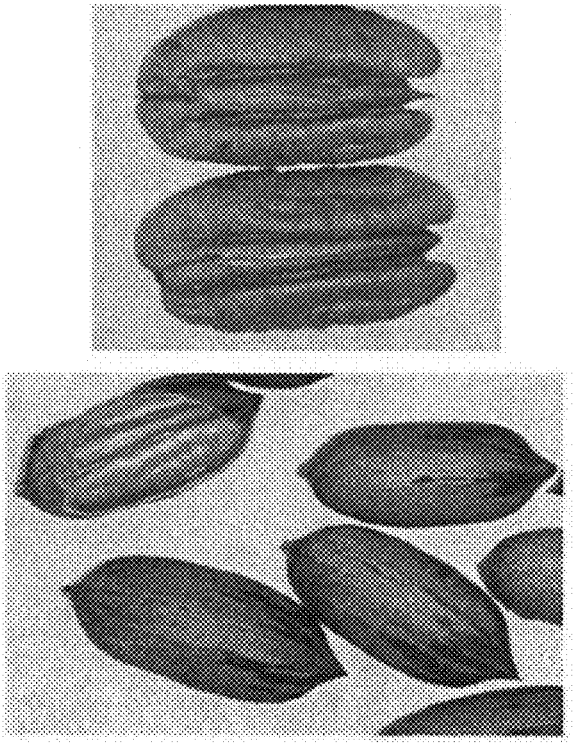

FIG. 2. Kernels (upper) and inshell nuts (lower) of 'ECLIPSE' pecan. Photographed in 2009.

Figure 3:
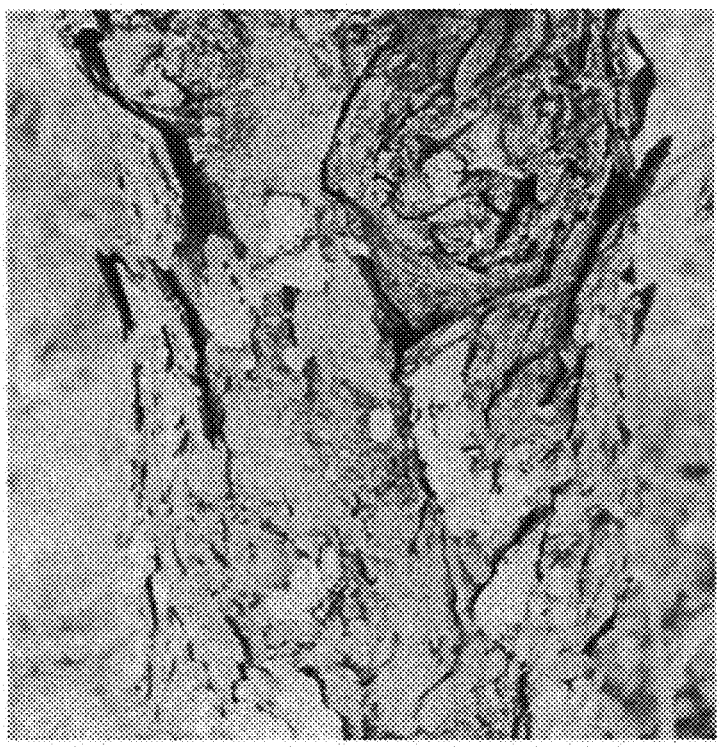

FIG. 3. Bark and trunk of 'ECLIPSE' pecan tree. Note the scaly large flaking bark pieces, similar to 'MOORE' non-patented and distinctive.

Figure 4:
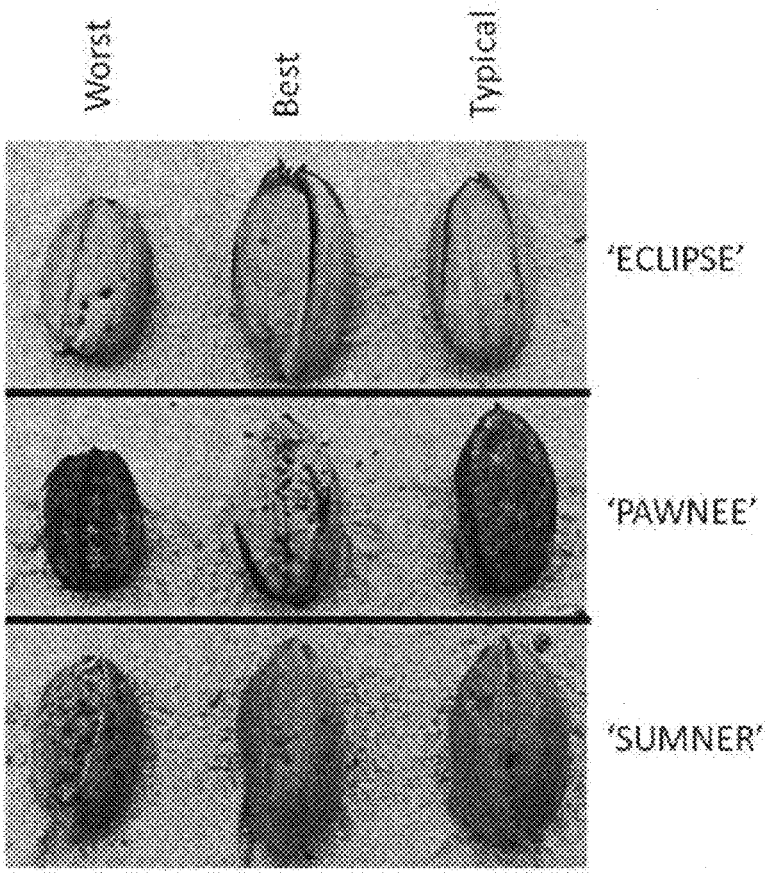

FIG. 4. Nut scab incidence on 'ECLIPSE' (top row), compared to 'Pawnee' non-patented (center row), and 'Sumner' non-patented (bottom row) on nearby trees in the same orchard treated similarly. Nuts were selected by Bill Goff on Sep. 12, 2009, to represent the nut with the worst scab on the tree (left column), least scab on the tree (center column), and typical scab on the tree (right column).

Figure 5:
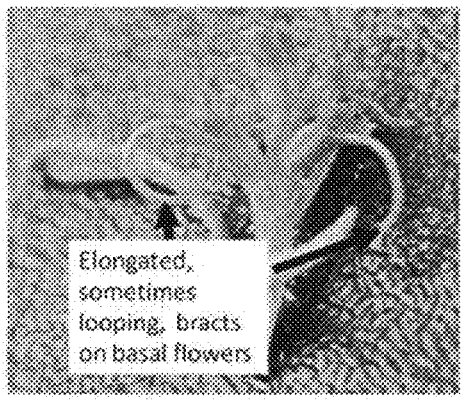
Figure 5:
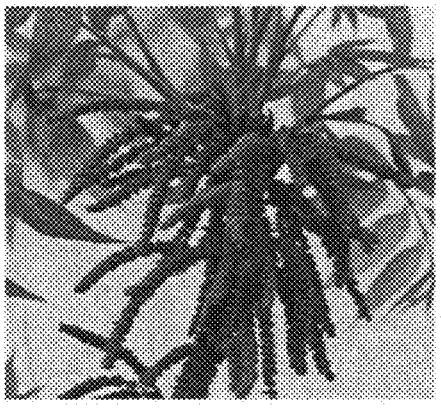

FIG. 5. Cluster of female flowers (left) of 'ECLIPSE' pecan and catkins bearing male flowers (right). Commonly and characteristically, one bract on one or more of the basal flowers in a cluster is four times or more longer than that of the other three bracts on the same flower. Photographed May, 2010.

BOTANICAL DESCRIPTION OF THE PLANT

Unless stated otherwise, the botanical description of 'ECLIPSE' is measured data in May, 2010, on the parent tree estimated to be 12 years old or on grafted trees less than one year after grafting. Observational data was in 2009-2010. The trees were grown in Pierce County, Ga. (USDA Zone 7b) under conditions which closely approximate commercial production, except spraying was minimal, with two sprays only applied in 2009. The range of day-time growing temperatures was 65-100 degrees F. The range of night-time growing temperature was 50-75 degrees F.

The plant is upright in growth habit, similar to 'Pawnee' non-patented, with a modified central leader tree form.

Lenticels are present on bark of twigs. Lenticels are irregular oval-shaped, 1-2 mm in length, and are gray. Lenticels are not observable on large branches and on trunk, which is covered with loose, flaking bark. Bark is gray.

The stems are green in the tender stage, then brown in the woody stage. The lateral winter buds are about 7 mm long, acute, somewhat 4-angled, valuate, moderate reddish brown and scurfy.

The peduncle is oval, green in tender stage and tan in mature stage.

The mature leaf is odd pinnate compound, deciduous, with dark green shade on upper surface, and light green on lower surface. The average length of a mature compound leaf is 36 cm, while the average width of a mature compound leaf is 20 cm. The average length of an individual leaflet is 13 cm, and the average width is 4.2 cm. The leaflet apex is acuminate and narrow. The leaflet base is oblique. The leaflet margin is serrate and the shape is elliptic and falcate, with absent lobes. The leaf arrangement on a stem is alternate, with leaflet venation pinnate. The average number of leaflets on a leaf is 11. The petiole and petiolules have slightly thickened bases. The petiole has a lightly fuzzy texture. The average petiole length is 18.7 cm and average petiole diameter is 2 mm.

The 'ECLIPSE' pecan is monoecious, anemophilous and protandrous. Pistillate flowers are borne on a determinate spike, with staminate flowers borne on a determinate pendulous catkin. There are commonly three to six individual pistillate flowers per spike, borne alternately on terminally-positioned spikes. The pistillate flower is symmetrical with no stamens and petals. The pedicels are sessile. The staminate flower or catkin is green with gold pollen. The average length of the catkin is 8.3 cm, average width 0.8 cm. These relatively short catkins are indicators of Type I or protandrous flowering habit where pollen is shed before stigmas are receptive. The flower has one pistil, with an oxblood color stigma. The flower has four bracts, which are green, linear lanceolate. Commonly and characteristically, one bract on one or more of the basal flowers in a cluster is four times or more longer than that of the other three bracts on the same flower.

The mature fruit is dehiscent. The average weight per nut in 2009, a year of small nut size in Georgia, was 7.4 g. The average nut length was 5.6 cm, while the average width was 2.2 cm. The nut length to width (width midway the length of the nut and across suture) is 1.83 cm. The nut shape is oblong to slightly obovate. The nut base shape is cuspidate and the nut apex is acute. The shell suture side is slightly elevated. The shell topography is somewhat rough. Shuck split was 90% on Sep. 12, 2009, compared to 10% on the same date on an adjacent 'Pawnee' non-patented tree in Pierce County, Ga. Shells are thin, approximately 0.62 mm, similar to 'Pawnee' non-patented. Shell markings are dark, bold and distinct near the tip, but are much less pronounced near the base of the nut.

The following are color descriptions of 'ECLIPSE', referencing The Royal Horticultural Society (R.H.S.) Colour Chart, published 1986.

Trunk: (Mature tree) RHS 202C.
Bark: RHS 202C.
Winter buds: RHS 174A.
Shoot: (Tender stage) RHS 138C.
Shoot: (Woody stage) RHS 202C.

Lenticels: RHS 201D.
Peduncle: (Tender stage) RHS 139C.
Foliage: (Upper surface) RHS 136B.
Foliage: (Lower surface) RHS 138A.
Petiole: RHS 144B.
Catkins: RHS 144B.
Stigma: RHS 175A.
Involucre: RHS 139C.
Bracts: RHS 139C.
Shell: RHS 165A.
Seed coat: RHS 164D.

What is claimed is:

1. A new and distinct variety of pecan tree named 'ECLIPSE', substantially as herein described and illustrated.

* * * * *